(12) United States Patent
Bezemer et al.

(10) Patent No.: US 6,528,056 B1
(45) Date of Patent: Mar. 4, 2003

(54) INHIBITION OF VIRAL INFECTION USING ANTIGEN-BINDING PROTEINS

(75) Inventors: Sandra Bezemer, Vlaardingen (NL); Leon Gerardus Joseph Frenken, Vlaardingen (NL); Johannes Joseph Wilhelmus deHaard, Vlaardingen (NL); Adrianus Marinus Ledeboer, Vlaardingen (NL); Cornelis Theodorus Verrips, Vlaardingen (NL)

(73) Assignee: Unilever Patent Holdings B.V., Vlaardingen (NL)

( * ) Notice: Subject to any disclaimer, the term of this patent is extended or adjusted under 35 U.S.C. 154(b) by 0 days.

(21) Appl. No.: 09/553,949

(22) Filed: Apr. 21, 2000

(30) Foreign Application Priority Data

Apr. 22, 1999 (EP) .............................. 99303117

(51) Int. Cl.⁷ ............................................ A61K 39/395
(52) U.S. Cl. ................................ 424/133.1; 424/135.1; 424/139.1; 424/147.1; 424/159.1; 435/236
(58) Field of Search .......................... 424/133.1, 135.1, 424/139.1, 147.1, 159.1; 435/236

(56) References Cited

FOREIGN PATENT DOCUMENTS

| | | |
|---|---|---|
| FR | 2 590 675 | 5/1987 |
| WO | WO91/08482 | 6/1991 |
| WO | WO 94/04678 | 3/1994 |
| WO | WO 94/25591 | 11/1994 |
| WO | WO99/23221 | 5/1999 |
| WO | WO99/46300 | 9/1999 |

OTHER PUBLICATIONS

Muyldermans, S., Journal of Molecular Recognition, (Mar.–Apr., 1999) vol. 12, No. 2, pp. 131–140.*
Martin et al, Protein Engineering, 10(5):607–614 (1997).
Williamson et al, Proc. Natl. Acad. Sci. USA, 90:4141–4145 (May, 1993).
Ghahroudi et al, Febs Letter, 414(3):521–526 (Sep., 1997).
Geller et al, J. Diary Sci., 81:895–900 (Apr., 1998).

* cited by examiner

Primary Examiner—Laurie Scheiner
(74) Attorney, Agent, or Firm—Morgan Lewis & Bockius LLP (57) ABSTRACT

A method of inhibiting viral infection using a monovalent antigen binding protein comprising a single domain binding unit capable of binding to a virus is described. Preferably the protein is a heavy chain variable domain derived from an immunoglobulin naturally devoid of light chains. Food, pharmaceutical and cosmetic products comprising such proteins are also described together with a method for selecting inhibiting proteins from a large population of mainly containing non-inhibiting, but infectious agent binding fragments.

7 Claims, 3 Drawing Sheets

INHIBITION OF VIRAL INFECTION USING ANTIGEN-BINDING PROTEINS

FIELD OF THE INVENTION

The present invention relates to the use of antigen binding proteins in a method of inhibiting the infectivity of viruses or other infectious agents, products and compositions comprising such proteins and methods for identifying and/or selecting antigen binding proteins capable of exhibiting such activity. In particular, the invention relates to a method for inhibiting viral infection using a monovalent antigen binding protein comprising a variable domain of a heavy chain derived from an immunoglobulin devoid of light chains, capable of binding to a virus.

BACKGROUND OF THE INVENTION

Antibodies are protein molecules belonging to a group of immunoglobulins generated by the immune system in response to an antigen. The structure of most antibody molecules is based on a unit comprising four polypeptides, two identical heavy chains and two identical light chains, which are covalently linked together by disulphide bonds. Each of these chains is folded in discrete domains. The C-terminal regions of both heavy and light chains are conserved in sequence and are called the constant regions, comprising one or more so-called C-domains. The N-terminal regions of the heavy and light chains, also known as V-domains, are variable in sequence and determine the specificity of the antibody. The regions in the variable domains of the light and heavy chains ($V_L$ and $V_H$ respectively) responsible for antigen binding activity are known as the hypervariable or complementary determining regions (CDR).

Immunoglobulins capable of exhibiting the functional properties of the four-chain immunoglobulins described above but which comprise two heavy polypeptide chains and which furthermore are devoid of light polypeptide chains have been described (WO 94/04678, Casterman et al, 1994). Fragments corresponding to isolated $V_H$ domains (hereinafter VHH) are also disclosed. Methods for the preparation of such antibodies or fragments thereof on a large scale comprising transforming a mould or yeast with an expressible DNA sequence encoding the antibody or fragment are described in patent application WO 94/25591 (Unilever).

The immunoglobulins described in WO 94/04678, which may be isolated from the serum of Camelids, do not rely upon the association of heavy and light chain variable domains for the formation of the antigen-binding site but instead the heavy polypeptide chains alone naturally form the complete antigen binding site. These immunoglobulins, hereinafter referred to as "heavy-chain immunoglobulins" are thus quite distinct from the heavy chains obtained by the degradation of common (four-chain) immunoglobulins or by direct cloning which contribute part only of the antigen-binding site and require a light chain partner for antigen-binding, thus forming a complete antigen binding site.

Antibodies or fragments thereof, have found application in a variety of uses where the specific nature of the antibody-antigen interaction can be used to advantage. These include such uses as diagnosis, therapy, immunoassays and purification processes. The use of antibodies, or fragments thereof, in inhibiting viral infection has received attention, for instance during active immunisation with inactivated virus preparations or viral antigens produced in recombinant cells or during passive immunisation by the administration of neutralising antibodies.

It has been reported in the literature that monovalent Fab antibody fragments can neutralise viruses. Cheung et al (1992), Journal of Virology, 66, 6714–6720, describe the production of the Fab domain of a rabies virus-neutralising antibody MAb-57 and further demonstrate that this monovalent fragment itself has virus-neutralising activity. Other publications also report the capability of human Fab monovalent antibody fragments to neutralise or inhibit viral activity (see for example, Williamson et al (1993), Proc. Natl. Acad. Sci. USA, 90, 4141–4145). Such methods are not suitable for wide scale industrial application as the cost of producing such classical antibody fragments renders the processes economically unfeasible.

An alternative approach to inhibiting viral replication using antibodies which has been described in the literature is to select antibodies to target enzymes produced by the virus. Martin et al, Protein Engineering, 10(5), 607–614 (1997) describes the use of a camelisedf VH antibody fragment to inhibit hepatitis C virus NS3 protease, thereby preventing cleavage of the viral poly-protein precursor.

Another industrial application in which economically viable solutions to the problem of viral infection are sought is the field of fermentation processing, particularly food processing.

Lactic acid bacteria: (LAB: Lactococci and Lactobacilli) play an important role in food fermentation processes such as the production of cheese or yoghurt. Often such fermentations are hampered by the sensitivity of the bacteria towards viruses, known as bacteriophage, which build up in these, often not aseptically performed, processes. A phage infection causes the LAB cells to lyse; during prolonged fermentations phage resistant cell populations can evolve, but this delay affects the production capacity severely, and the disturbed process yields a product of low quality. Sometimes the process has to be stopped prematurely, with complete loss of the batch of milk.

To date, the phage problem has mainly been approached by taking special precautions with respect to hygiene at the production facility, but this causes additional time delays. Another solution which has been proposed is the use of resistant LAB strains, but the regular appearance of adapted forms of bacteriophage forces the strains used to be changed from time to time in a procedure known as culture rotation. This has the disadvantage of requiring labour intensive monitoring of the production facilities and medium for the presence of phage and requires the availability of several sets of cultures with the same functional attributes, differing only in phage sensitivity. There therefore remains considerable commercial interest in the further development of methods for combating LAB phage infection.

One method, proposed by Geller et al (1998), J. Dairy Sci., 81, 895–900, involves the use of colostrum from cows immunised with lactococcal phage as a source of phage-neutralising (polyclonal) antibodies to prevent lytic infection of Lactococcus lactis in fermentations of phage-contaminated milk. This method does not provide a commercially viable solution to the problem, however. Not only is it extremely economically unattractive to produce antibodies in this way but furthermore, the addition of colostrum to milk does not have regulatory approval.

An alternative approach, which makes use of multivalent, multispecific antigen binding proteins comprising a polypeptide comprising in series two or more single domain binding units, preferably variable domains of a heavy chain derived from an immunoglobulin naturally devoid of light chains, to reduce the infectivity of LAB phages by cross-linking or agglutination is exemplified in the Applicant's co-pending patent application number PCT/EP98/06991, filed Oct. 26, 1998.

There remains a continuing need for the development of improved methods of inhibiting or neutralising viral infection. In particular, there remains continuing interest in development of methods which can be applied economically on a scale appropriate for industrial use.

SUMMARY OF THE INVENTION

Accordingly, the invention provides in one aspect a method of inhibiting viral infection using a monovalent antigen binding protein comprising a single variable domain binding unit, or a functional equivalent thereof, capable of binding to a virus.

In another aspect the invention provides the use of a monovalent antigen binding protein comprising a single variable domain binding unit or a functional equivalent thereof capable of binding to a virus in inhibiting viral infection.

The invention also provides the use of a monovalent antigen binding protein comprising a single variable domain binding unit or a functional equivalent thereof capable of binding to a virus in the preparation of a medicament for inhibiting viral infection.

Also provided are monovalent antigen binding proteins comprising a single variable domain binding unit capable of binding to a virus, nucleotide sequences encoding such proteins, cloning and expression vectors comprising such nucleotide sequences, host cells transformed with vectors comprising such nucleotide sequences, and food, cosmetic and pharmaceutical products comprising such proteins.

In a further aspect, the invention provides a method for selecting an antigen binding protein capable of inhibiting viral infection of a host cell comprising the steps of:
  i) complexing an antigen binding protein with a target virus,
  ii) exposing the antigen binding protein-virus complex of step (i) to an excess of host cells,
  iii) removing the host cells and any associated antigen binding protein-virus complex,
  iv) capturing antigen binding protein-virus complex not taken up by the host cells in step (ii) with virus specific ligands to separate virus specific antigen binding proteins from non-binding proteins.

The invention also provides a method for identifying an antigen binding protein capable of inhibiting bacteriophage infection of a lactic acid bacterial cell host comprising the steps of:
  i) culturing of bacterial host cells in the presence of antigen binding protein and bacteriophage,
  ii) assaying said culture for active cell growth manifest in a change in pH of the culture growth medium.

As used herein, a single variable domain binding unit means an immunoglobulin variable domain or a functional equivalent thereof which forms a complete antigen binding site. This may be derived from natural sources or synthetically produced. The terms 'immunoglobulin' and 'antibody' are used synonymously throughout the specification, unless indicated otherwise.

A 'functional equivalent' of an imunoglobulin variable domain is any homogolous protein molecule which has similar binding specificity. A functional equivalent may be characterised by an insertion, deletion or substitution of one or more amino acid residues in the sequence of the immunoglobulin variable domain. Suitably, the amino acid sequence of the functional equivalent has at least 60% similarity, preferably at least 80%, more preferably at least 90% similarity to the amino acid sequence of the immunoglobulin variable domain.

Inhibition of viral infection includes but is not limited to inhibition of infection by blocking essential sites on the viral particle, such as the receptor binding protein of the virus by which the virus attaches to the host cell during the first step of infection. Inhibition may be total or partial. The terms 'inhibit' and 'neutralise' are used synonomously herein.

The term 'virus' includes within its scope viruses, which infect bacterial host cells, known as bacteriophages. Binding to a virus includes binding to one or more molecules located at the surface of the virus particle.

The present invention may be more fully understood with reference to the following description when read together with the accompanying drawings in which.

DETAILED DESCRIPTION OF THE INVENTION

The invention is based on the finding that a monovalent antigen binding protein comprising a single variable domain binding unit capable of binding to a virus can advantageously be used to inhibit infection of a host cell by the virus. High production levels and ease of downstream processing permits such antigen binding proteins to be applied in industrial processes and products economically and efficiently.

As discussed above, antibody based methods for inhibiting viral infection which have previously been described in the literature have relied either on cross-linking mediated via multivalent constructs or have made use of larger fragments derived from 'classical' antibodies, such as Fab fragments, to block the receptor binding protein of the virus, hence inhibiting its ability to infect the host cell.

Surprisingly, the present inventors have found that much smaller monovalent antigen binding proteins comprising a single variable domain are effective in inhibiting viral infection. This would not have been predicted from the prior art teaching as the smaller size of these proteins might have been expected to have rendered them less effective in hindering binding of the virus to the host cell. Moreover, it would be expected that multivalent antigen binding proteins would be more effective due to the agglutination of infectious particles. To date, only the recognition of simple protein antigens with such binding proteins has been reported. There has been no suggestion that complex systems such as viruses could be detected and inhibited using single domain binding units.

The invention is applicable to the use of any immunoglobulin variable domain, which forms a complete antigen binding site. The immunoglobulin may be derived from natural sources or synthetically produced. Preferably, the invention relates to the use of heavy chain variable domains derived from an immunoglobulin devoid of light chains, most suitably from an immunoglobulin naturally devoid of light chains such as are obtainable from lymphoid cells, especially peripheral blood lymphocytes, bone marrow cells or spleen cells derived from Camelids as described in WO 94/04678 (Casterman et al) discussed above.

It will be appreciated that heavy chain variable domains derived from other immunoglobulins modified ('camelised') to enable them to function as monovalent binding domains in the same way as the heavy chain variable domains derived from Camelids may also suitably be used according to the invention.

An advantage of using single domain binding units which are heavy chain variable domains derived from Camelids is that they can readily and conveniently be produced economically on a large scale, for example using a transformed lower eukaryotic host as described in WO 94/25591 (Unilever). A major advantage of the described production system is the low degree of impurities present in the secreted fraction, thereby enabling simple down stream processing procedures for purification. A further advantage, particularly when applications in food processing are contemplated, is that such heavy chain variable domains are extremely heat stable, allowing pasteurisation or other heat treatments without loss of antigen binding capacity.

The invention is applicable to both prokaryotic and eukaryotic host cells. For therapy of humans or animals, target viruses of interest include pathogenic viruses such as those which belong to the family of Human Immunodeficiency Viruses. Other viral infections to which the invention is applicable include such food-born viruses as Hepatitis viruses (especially Hepatitis A virus), Rotavirus and the small round Structured viruses (SRSV), such as Norwalk virus (see Food Science and Technology Today, II(1), 49–51, 1997). In the area of production crops, viruses pathogenic to plants such as Citrus tristeza virus (CTV), Tobacco mosaic virus (TMV), Potato virus Y (PVY), Lettuce necrotic yellows virus (LNYV), Tomato spotted wilt virus (TSWV), Clover wound tumour virus (CWTV), Cauliflower mosaic virus (CaMV), Cowpea mosaic virus (CPMV), Soil-borne wheat furiovirus (SBWMV), Wheat yellow mosaic bymovirus (WYMV) and Wheat spindle streak mosaic virus (WSSMV) are important targets for neutralisation or inhibition.

Single domain binding units such as heavy chain variable domains recognising plant viruses can be cloned and expressed in plants using methods equivalent to conventional cloning and expression of (modified) viral proteins, to protect these plants viruses. By using the appropriate targeting signals known in the art, the expression and translocation of the VHH's can be regulated in such a way that organelle or in the extracellular matrix.

The invention is of particular use in industrial fermentation processes, for example neutralising or inhibiting the infectivity of lactococcal bacteriophage, thereby preventing lytic infection of *Lactococcus lactis*. By inhibiting the infectivity of lactococcal bacteriophages, the invention affords the possibility of avoiding having to adopt the various cost affecting measures described above. The antigen binding proteins can be used in a cleaning product, which removes phage present in the production system. Alternatively, they can be added to milk contaminated with bacteriophage, as is shown in Example 3 below, which can be fermented to a high quality product without any delay in the production. The standard addition of such antigen binding proteins to milk would be one way in which it might be possible to abolish monitoring for the presence of phage.

Lactic acid bacteria play an important part in fermentation of many other food products in addition to dairy products. It will be appreciated that the invention is not restricted to use in inhibiting LAB phage infection in dairy fermentation processes but extends also to use in any process which makes use of lactic acid bacteria fermentation. Suitable fermented food products and the associated lactic acid bacteria are listed in tables 1a–1b below (see Biotechology, Vol 5, Chapter 1–8).

TABLE 1a

Main functional lactic acid bacteria in European Fermented Foods

| PRODUCT NAME | SUBSTRATE | MAIN LACTIC ACID BACTERIA |
|---|---|---|
| Baked Goods | Wheat | *Lactobacillus plantarum* |
| | | acidophilus |
| | | delbrueckii |
| | | brevis |
| | | buchneri |
| | | fermentum |
| | | s.francisco |
| Wine & Brandy | Grapes | *Leuconostoe gracile* |
| | | oenos |
| | | *Lactobacillus plantarum* |
| | | casei |
| | | fructivorans |
| | | hilgardii |
| | | brevis |
| | | *Pediococcus cerevisiae* |
| Cheese & Dairy Products | Milk | *Brevibacterium linens* |
| | | *Lactococcus lactis* |
| | | cremoris |
| | | *Lactobacillus casei* |
| | | helveticus |
| | | bulgaricus |
| | | plantarum |
| | | *Leuconostoc cremoris* |
| | | *Pediococcus acidilactici* |
| | | pentosaceus |
| | | *Sreptococcue thermophilus* |
| | | *Enterococcus faecium* |
| Fermented vegetables/fruits | Cabbage & Cucumbers | *Lactobacillus brevis* |
| | | plantarum |
| | | *Leuconostoc mesenteroides* |
| | | *Pediococcus cerevisiae* |
| | Olives | *Lactobacillus plantarum* |
| | | paracasei |
| | | brevis |
| | | delbrueckii |
| | | Streptococcus sp. |
| | | Pediococcus sp. |
| | | Leuconostoc sp. |
| Sausages | Meat | *Lactobacullus curvatus* |
| | | lactis |
| | | plantarum |
| | | sake |
| | | *Pediococcus acidilactici* |
| | | pentocaceus |
| | | *Micrococcus caseolyticus* |

TABLE 1b

Main functional lactic acid bacteria in Indigenous Fermented Foods

| PRODUCT NAME (Country) | SUBSTRATES | MAIN LACTIC ACID BACTERIA |
|---|---|---|
| Banku (Ghana) | Maize, cassava | Lactic acid bacteria |
| Burukutu (Nigeria) | Sorghum, cassava | Lactic acid bacteria |
| Busa (Egypt) | Rice, millet | Lactobacillus sp. |
| Dawadawa (Nigeria) | Locust bean | Lactic acid bacteria |
| Dosai (India) | Black gram and rice | *Lauconostoc mesenteroides* |
| Hamanatto (Japan) | Whole soybean, | Streptococcus sp. |

TABLE 1b-continued

Main functional lactic acid bacteria in Indigenous Fermented Foods

| PRODUCT NAME (Country) | SUBSTRATES | MAIN LACTIC ACID BACTERIA |
|---|---|---|
| | wheat flour | Pediococcus sp. |
| Idli (India) | Rice, black gram | Leuconostoc mesenteroides |
| Kecap (Indonesia) | Soybean, wheat | Lactobacillus sp. |
| Kimchi (Korea) | Vegetables (seafood, nuts) | Lactic acid bacteria |
| Kishk (Egypt) | Wheat, milk | Lactic acid bacteria |
| Mshewu (S. Africa) | Maize | *Lactobacillus delbrueckii* |
| Miso (China, Japan) | Rice and soybean | Lactobacillus sp. |
| | Rice and cereals | Lactobacillus sp. |
| Ogi (Nigeria) | Maize | Lactic acid bacteria |
| Puto (Philippines) | Rice | Lactic acid bacteria |
| Sorghum beer (S. Africa) | Sorghum, maize | Lactic acid bacteria |
| Soybean milk (Asia) | Soybean | Lactic acid bacteria |
| Soy sauce (Asia) | Soybean and wheat | Lactobacillus sp. Pediococcus sp. |
| Tarhana (Turkey) | Wheat and milk | Lactic acid bacteria |

The invention further provides nucleotide sequences coding for the monovalent antigen binding proteins capable of inhibiting the commonly occurring lactococcus bacteriophage P2. The inhibiting binding domains were identified with a high-throughput screening assay, which allows the discrimination of inhibiting from non-inhibiting binding proteins. The involved binding site on phage P2 was characterised by electron microscopy with binding domain fragments conjugated to gold particles. In addition, the cross-reactivity against members of the same family and of other families of bacteriophage was analysed in more detail.

Particular heavy chain variable domains (referred to hereinafter as VHH fragments) of use according to the invention in inhibiting lactococcus bacteriophage P2 comprise the seqences:

the identification of inhibiting fragments are yeast display (WO 94/01567 from Unilever) or phage display.

A preferred method to enrich for inhibiting binding domains applicable to the single variable domain binding units described herein, is based on the removal of clones that expose non-inhibiting binding domains, through capture of a complex of the binding domain and the infectious agent of interest by host cells via a receptor protein to which the non-inhibited infectious agent can bind.

Viral infection inhibiting antigen binding proteins according to the invention may be prepared by transforming a host by incorporating a gene encoding the polypeptide as set forth above and expressing said gene in said host.

Suitably the host or hosts may be selected from prokaryotic bacteria, such as Gram-negative bacteria, for example *E. coli,* and Gram-positive bacteria, for example *B. subtilis* and in particular lactic acid bacteria, lower eukaryotes such as yeasts, for example belonging to the genera Saccharomyces, Kluyveromyces, Hansenula or Pichia, or moulds such as those belonging to the genera Aspergillus or Trichoderma.

Preferred hosts for use in connection with the present invention are the lower eukaryotic moulds and yeasts, and in particular the lactic acid bacteria, which can be directly used for the fermentation of milk.

Techniques for synthesising genes, incorporating them into hosts and expressing genes in hosts are well known in the art and the skilled person would readily be able to put the invention into effect using common general knowledge.

Proteins for use according to the invention may be recovered and purified using conventional techniques such as affinity chromatography, ion exchange chromatography or gel filtration chromatography.

The binding activity of the binding proteins according to the invention may conveniently be measured by standard techniques known in the art such as enzyme-linked immunoadsorbant assay (ELISA), radioimmune assay (RIA) or by using biosensors. The inhibiting capacity may be examined

```
VHH#1                                                       (SEQ. ID NO. 1)

QVQLQESGGG LVQAGGSLRL SCTASRRTGS NWCMGWFRQL AGKEPELVVA LNFDYDMTYY

ADSVKGRFTV SRDSGKNTVY LQMNSLKPED TAIYYCAARS GGFSSNRELY DGWGQGTQVT VSS

VHH#2                                                       (SEQ. ID NO. 2)

QVQLQESGGG LVQAGGSLRL SCTASRRTGS NWSMGWFRQL AGKEREFVVA LNLDYDIPYY

ADSVKGRFTV STDSGKNTVY LQMNSLKPED TAIYFCAARS GGFSSNRTYY DYWGQGTQVT VSS

VHH#3                                                       (SEQ. ID NO. 3)

QVQLQQSGGG LVQRGGSLRL SCTASRRTGS NWSMGWFRQF AGKEPDLLVA LNLDYDVPYY

ADSVKGRFTV SGDSGKNTVY LQMNNLKPED TAIYYCAARS GGFSSNRALY DGWGQGTQVT VSS
```

The invention also provides host cells and expression vectors enabling high level production and secretion of the binding proteins.

Heavy chain variable domains derived from an immunoglobulin naturally devoid of light chains having a determined antigen specificity may conveniently be obtained by screening expression libraries of cloned fragments of genes encoding Camelid immunoglobulins generated using conventional techniques, as described, for example, in WO 94/04678 and Example 1. Suitable methods to enrich for binding domains recognising the infectious agent, thereby limiting the numbers of clones which have to be screened for by the inhibition of plaque formation of phage and viruses, or by a method, which reveals continued cell growth as a measure for resistance against infection. In the case of lactococcus bacteriophage, the high throughput screening assay described in this application, or in an acidification experiment by the fermentation of milk is particularly applicable.

Antigen binding proteins capable of binding to a virus according to the present invention may conveniently be added to food or cosmetic compositions by methods conventional in the art to give products which are protected against infection by the particular virus. Alternatively, the antigen binding proteins according to the invention may be formulated into pharmaceutical compositions with pharmaceutically acceptable carriers and/or excipients and optionally other pharmaceutically or cosmetically active ingredients using techniques well known in the art.

The following examples are provided by way of illustration only. Techniques used for the manipulation and analysis of nucleic acid materials were performed as described in Sambrook et al, Molecular Cloning, Cold Spring Harbor Press, New York, 2nd Ed. (1989), unless otherwise indicated. Phages were isolated and propagated according to the methods described by Moineau et al, Canadian Journal of Microbiology 38/9, 875–882 (1992).

$V_HH$ denotes heavy chain variable domain of heavy chain antibodies.

Restriction sites are underlined.

EXAMPLES

Example 1

Induction of a Humoral Immune Response in Llama

A male llama was immunised with bacteriophage P2 of *Lactococcus lactis* in oil emulsion (1:9 V/V, antigen in water: Specol (Bokhout et al (1981), Immunol. Immunopath., 2, 491–500; Bokhout et al (1986), Infect. Dis., 161–168) subcutaneously and intramuscularly. Per immunisation site 0.75–1.5 ml water in oil emulsion was injected containing 200 µg phage protein (approx. $6*10^{13}$ pfu). Immunisations were performed according to the following time schedule: the second immunisation was performed three weeks after the first injection, and the third immunisation two weeks after the second one. The immune response was followed by titration of serum samples in ELISA with bacteriophage immobilised on Nunc maxi-sorb plates (coat solution $10^{10}$ pfu/ml diluted in phosphate buffered saline). After incubation with serum, the bound llama antibodies were detected with polyclonal rabbit-anti-llama antiserum (obtained via immunising rabbits with llama immunoglobulines purified via ProtA and ProtG columns; ID-DLO) and swine-anti-rabbit immunoglobulines (DAKO) conjugated to horse radish peroxidase. Finally the peroxidase enzyme-activity was determined with tetramethylbenzidine and ureaperoxide as substrate and, after termination of the reaction by adding $H_2SO_4$, the optical density was measured at 450 nm.

Example 2

Cloning, Selection and Screening of Llama $V_HH$ Fragments Neutralising *Lactococcus lactis* Bacteriophage P2

2.1 Isolation of $V_HH$ fragments against *Lactoccus lactis* bacteriophage P2

From the llama, positively responding against bacteriophage P2 as tested in ELISA, a blood sample of about 200 ml was taken and an enriched lymphocyte population was obtained via centrifugation on a Ficoll (Pharmacia) discontinuous gradient. From these cells, total RNA was isolated by guanidium thiocyanate extraction (e.g. via the method described by Chomczynnski and Sacchi (1987), Analytical Biochem., 162, 156–159. After first strand cDNA synthesis using MMLV-RT (Gibco-BRL) and random oligonucleotide primers (Pharmacia), DNA fragments encoding $V_HH$ fragments and part of the long or short hinge region were amplified by PCR using specific primers:

```
                                                        (SEQ. ID NO. 4)
                    PstI
V_H - 2B  5'-AGGTSMARCTGCAGSAGTCWGG-3'
S = C and G, M = A and C, R = A and G, W = A and T,
                                                        (SEQ. ID NO. 5)
                    HindIII
Lam-07  5'-AACAGTTAAGCTTCCGCTTGCGGCCGCGGAGCTGGGGTCTTCGCTGTGGTGCG-3'
(short hinge)
                                                        (SEQ. ID NO. 6)
                    HindIII
Lam-08  5'-AACAGTTAAGCTTCCGCTTGCGGCCGCTGGTTGTGGTTTTGGTGTCTTGGGTT-3'
(long hinge)
```

The DNA-fragments generated by PCR were digested with PstI (coinciding with codon 4 and 5 of the $V_HH$ domain, encoding the amino acids L–Q) and HindIII (introduced at the 5' end of the hinge specific oligonucleotide primers, coinciding with the amino acid sequence S-L-T), and cloned in the phagemid vector pUR4676 (identical to pHEN1 (Hoogenboom et al, Nucleic Acids Res., (1990), 19, 4133–4137), containing the lacI element as described by Orum et al, Nucleic Acid Res., (1993), 21, 4491–4498) as gene-fragments encoding the $V_HH$-domain including the hinge region fused to the geneIII protein of the *E. coli* bacteriophage M13, thereby enabling display of the antibody fragment on the surface of the filamentous phage (McCafferty et al (1990), Nature 6, 552–554).

2.2 Enrichment of lactococcus bacteriophage binding $V_HH$ domains via phage display methodology I) A display library with $1×10^7$ clones, of which 75% contained a complete $V_HH$ encoding insert, was constructed in phagemid vector pUR4676. Phage particles exposing $V_HH$ fragments were prepared by infection of *E. coli* cells harbouring the phagemid with helperphage VCS-M13 (Marks et al (1991), J. Mol. Biol., 222, 581–597). By precipitation of phage from the culture supernatant with PEG6000, free $V_HH$ fragments were removed, thereby avoiding a disturbing competition for binding to antigen between phage bound and free $V_HH$ domains.

II) Phage antibodies binding to lactococcus bacteriophage P2, immobilised on maxisorp immunotubes, were selected from the library via the biopanning procedure (McCafferty et al (1990), Nature, 6, 552–554). After an extensive washing procedure, *E. coli* phage was eluted from the tube with 0.1 M triethylamine (Baker) by disruption of the antigen-antibody binding with this alkaline shock. After neutralisation with 0.5 volume of 1 M Tris-HCl pH7.4, phage was rescued by transfection into the *E. coli* host TG1. A renewed selection was performed with phage prepared from the transfected population of *E. coli* bacteria as was described before. Alternatively, 'in solution' capture of *E. coli* phage exposing lactococcus phage specific antibody fragments was performed with in vitro biotinylated bacteriophage P2. Antigen-antibody complexes and associated phage particles were pulled out of the solution with streptavidin coated magnetic beads (Dynal) (see Hawkins et al (1992), J. Mol. Biol., 226, 889–896). After washing, *E. coli* phage was eluted with triethylamine as described before.

Individual *E. coli* clones obtained after the two rounds of selection were grown in wells of microtiter plates, and the production of $V_HH$ fragments was induced by the addition of isopropyl-β-D-thiogalactopyranoside (IPTG, 0.1 mM). After 16 hours of growth, the culture supernatant of the clones was analysed in ELISA for the presence of $V_HH$ fragments, which specifically bind to immobilised bacteriophage P2. Bound $V_HH$ fragments were detected with rabbit anti-llama $V_HH$ polyclonal antibodies followed by incubation with goat anti-rabbit polyclonal antibodies conjugated to horse radish peroxidase (BIORAD), or with mouse monoclonal anti-myc antibody followed by incubation with polyclonal rabbit-anti-mouse conjugated to horse radish peroxidase (DAKO).

2.2.1 Alternative enrichment method

Following the method of Example 2.2(I) above, a library of phage bound VHH domains may be prepared. After incubation of the *E. coli* phage with in vitro biotinylated lactococcus bacteriophage P2 for two hours, *E. coli* phage clones exposing non-neutralising, but phage P2 specific VHH fragments may be captured with an excess of host cells from strain *L. lactis*. The *E. coli* phage particles complexed to biotinylated phage P2 via their exposed VHH fragments, but which are not bound to *L. lactis* (and thereby potentially neutralising), may be captured from solution with virus specific ligands such as streptavidin coated magnetic beads, and thus separated from *E. coli* phage not bound via their exposed VHH fragment to phage P2. After elution with a pH-shock (0.1 M triethylamine), the phage population enriched for neutralising VHH domains may be rescued by infection of *E. coli* host cells.

As an alternative method, unlabeled phage P2 can be used instead of biotinylated phage for binding to VHH-exposed *E. coli* phage. After capture of clones exposing non-neutralising VHH fragments with *L. lactis,* a population of clones displaying neutralising binding domain proteins can be captured from solution with monoclonal or polyclonal antibodies directed against *L. lactis* bacteriophage P2, which were immobilised on a solid surface or coupled to a matrix.

Individual *E. coli* clones may be grown in wells of microtiter plates, and the production of VHH fragments induced by addition of IPTG (0.1 mM). Culture supernatants containing free VHH domains may be tested in ELISA for binding to *L. lactis* bacteriophage P2 using the myc-TAG for detection and for their inhibiting capacity in the high throughput assay using the techniques described above.

2.3 Development of a high-throughput screening assay for the identification of bacteriophage neutralising $V_HH$ fragments The phage neutralising capacity of the $V_HH$ fragments was demonstrated by a continued growth of the host cell *L. lactis*. As measure for cell growth the acidification in milk was followed with the included pH indicator bromophenol red, which changes from purple-red (pH is 6.5 to 7.0) at the start of cultivation to yellow (pH 4.5 to 5.0) after 8 to 15 hours of growth. 50 µl supernatant of individual clones derived from the selections with *E. coli* or *S. cerevisiae* was mixed with 50 µl phage solution ($2*10^9$ pfu/ml diluted in semi-skimmed milk supplemented with 0.35% peptone, 0.35% yeast extract, 1% glucose, 0.8% Polymixin B) in a well of a microtiter plate. Subsequently, 100 µl of *L. lactis* cells (50-fold diluted overnight culture in semi-skimmed milk medium described before, supplemented with 2% bromophenol red). After 8 to 15 hours of incubation at 30° C., ten neutralising antibodies out of 285 analysed $V_HH$ fragments were identified by the change in colour (yellow). Three of these were characterised in detail (see section 2.6 and further).

2.4 Sequences of bacteriophage neutralising $V_HH$ fragments

As indicated in the preceding paragraphs anti-LAB-phage $V_HH$ fragments were obtained, which are capable to neutralise lactococcus bacteriophage P2. The sequences of three of such fragments are presented below:

```
VHH#1                                                   (SEQ. ID NO. 1)
(cloned in E. coli phagemid vector pUR3827 and in S. cerevisiae
episomal plasmid pUR3834):

QVQLQESGGG LVQAGGSLRL SCTASRRTGS NWCMGWFRQL AGKEPELVVA LNFDYDMTYY

ADSVKGRFTV SRDSGKNTVY LQMNSLKPED TAIYYCAARS GGFSSNRELY DGWGQGTQVT VSS

VHH#2                                                   (SEQ. ID NO. 2)
(in E. coli plasmid pUR3828 and in S. cerevisiae episomal plasmid
pUR3835):

QVQLQESGGG LVQAGGSLRL SCTASRRTGS NWSMGWFRQL AGKEREFVVA LNLDYDIPYY

ADSVKGRFTV STDSGKNTVY LQMNSLKPED TAIYFCAARS GGFSSNRTYY DYWGQGTQVT VSS

VHH#3                                                   (SEQ. ID NO. 3)
(in E. coli plasmid pUR3829 and in S. cerevisiae episomal plasmid
pUR3836):
```

-continued
QVQLQQSGGG LVQRGGSLRL SCTASRRTGS NWSMGWFRQF AGKEPDLLVA LNLDYDVPYY

ADSVKGRFTV SGDSGKNTVY LQMNNLKPED TAIYYCAARS GGFSSNRALY DGWGQGTQVT VSS

Example 3
The Efficiency of $V_HH$ Fragments in neutralising *Lactococcus lactis* Bacteriophage P2

3.1 Recloning in episomal plasmid system for production of $V_HH$ fragments in *S. cerevisiae*

The $V_HH$ encoding genes of clones VHH#1, VHH#2 and VHH#3 were digested with PstI (present at the 5' end of the $V_HH$ gene and introduced by primer VH-2B (SEQ. ID. NO. 1)) and BstEII (naturally occurring at the 3' end of most $V_HH$ genes) and BstEII from the *E. coli* phagemid vectors pUR3827, pUR3828 and pUR3829 respectively, and cloned in the episomal *S. cerevisiae* secretion plasmid pUR4547, thereby obtaining pUR3834, pUR3835 and pUR3836 respectively. Plasmid pUR4547 (deposited as CBS100012), with an Ori for autonomous replication in *S. cerevisiae*, enables the production via the inducible Gal7 promotor; secretion is accomplished by fusing the SUC leader sequence (Harmsen et al (1993), Gene, 125, 115–123) to the amino terminus of the $V_HH$ product. The production was examined by analysis of the medium fraction obtained after 48 hours of cultivation at 30° C. from 5 clones of each construct on a Coomassie blue stained polyacrylamide gel.

Plasmid pUR4547 was deposited under the Budapest Treaty at the Centraal Bureau voor Schimmelcultures, Baarn on Aug. 18, 1997 with deposition number: CBS 100012. In accordance with Rule 28(4) EPC, or a similar arrangement from a state not being a contracting state of the EPC, it is hereby requested that a sample of such deposit, when requested, will be submitted to an expert only.

3.2 Construction of stable $V_HH$ producing clones of *S. cerevisiae* by multi-copy integration in the genome Integration of the genes encoding the antibody fragments for establishing stable secreting *S. cerevisiae* cell lines was accomplished by homologous recombination into the yeast genome. By choosing a multi-copy locus, i.e. the ribosomal DNA-(rDNA) locus containing between 100 and 150 rDNA units, the insertion of multiple copies was forced, thereby yielding high production levels of antibody fragment. The $V_HH$ gene of clone #1 was digested with the restriction enzymes SacI (located before the SUC leader sequence) and HindIII (located behind the stopcodon of the $V_HH$ gene) and HindIII from the episomal secretion plasmid pUR3834, and cloned in the integration plasmid pUR2778 (Guiseppin et al (1991), WO 91/00920; Driedonks et al (1995), Yeast, 11, 849–864). This plasmid contains the Gal7 promoter for inducible expression of the $V_HH$ gene product (without tags for identification or purification), the selectable markers bla (β-lactamase) to discriminate transformants in *E. coli* by resistance to the antibioticum ampicillin and Leu2d (β-isopropylmalate dehydrogenase) for propagation of transformed *S. cerevisiae*, an *E. coli* origin of replication, and finally the flanking homologous sequences for recombination into the genome of *S. cerevisiae*. Transformants in *E. coli* containing constructs with the $V_HH$ gene were identified by restriction enzyme analysis. Plasmid purified with the Nucleobond AX100 kit was used for transformation of *Saccharomyces cerevisiae* strain VWK18gall::URA3 with the lithiumacetate procedure (Gietz and Schiestl (1995), Meth. Mol. Cell. Biol., 5, 255–259). At least 10 individual clones were chosen for production in 50-ml cultures; the medium fraction with the secreted $V_HH$ fragments was analysed on a Coomassie blue stained SDS PAGE gel. The clone producing antibody fragment VHH#1 most efficiently was coded pUR3858 and it was used for production in a 10-L fermentor. The medium fraction containing the antibody fragment was concentrated by ultrafiltration and further purification was accomplished by means of ion-exchange chromatography (Mono-S-sepharose, Pharmacia). The amount of purified antibody was determined by an OD280 measurement, the micro BCA method, and confirmed by the analysis on a Coomassie stained SDS PAGE gel.

3.3 Neutralisation measured by the inhibitory effect on plaque formation

To test the neutralising effect of the anti-phage P2 $V_HH$, the reduction in the phage titers was determined. Therefore antibody fragments, produced by *S. cerevisiae* containing plasmid pUR3834 encoding the neutralising anti-LAB phage VHH#1, or plasmid pUR3831 encoding the LAB phage binding but non-neutralising VHH#4, or construct pUR3850 (PCT/EP98/06991) encoding the neutralising bihead molecule VHH#4-#5, made up of the non-neutralising $V_HH$-fragments VHH#4 and VHH#5 (of the following sequences:

VHH#4: (SEQ. ID NO. 7)

QVQLQESGGG LVQPGGSLRL SCVVSGEGFS NYPMGWYRQA

PGKQRELVAA MSEGGDRTNY ADAVKGRFTI SRDNAKKTVY

LQMSSLKPED TAVYYCNAAR WDLGPAPFGS WGQGTQVTVS S

VHH#5: (SEQ. ID NO. 8)

QVQLQESGGG LVQPGGSLRL SCAVSGAPFR ESTMAWYRQT

PGKERETVAF ITSGGSKTYG VSVQGRFTIS RDSDRRTVLL

QMMNLQPEDT AVYYCHRALS NTWGQGIQVT VSS where purified as described before. From the monovalent fragments 100 and 5 μg, and 5 and 0.25 μg of the bivalent fragment, were mixed with $5.0*10^8$ phage P2 in 1 ml total volume (diluted in phage buffer: 20 mM Tris-HCl pH 7.4, 100 mM NaCl, 10 mM $MgSO_4$) and incubated for 0.5 hours at 37° C. From this incubation mixture 100 μl undiluted solution, $10^{-2}$, $10^{-4}$ and $10^{-6}$ diluted solution was added to 100 μl of a culture of *Lactococcus lactis* subsp. *cremoris* LM0230 ($1*10^9$ cfu/ml), which was grown overnight in M17. After the addition of 3 ml of M17 top-agar, the mixture was poured on a plate of M17 containing 0.5% glucose and 10 mM $CaCl_2$. Plates were incubated overnight at 30° C.

Figure 1:
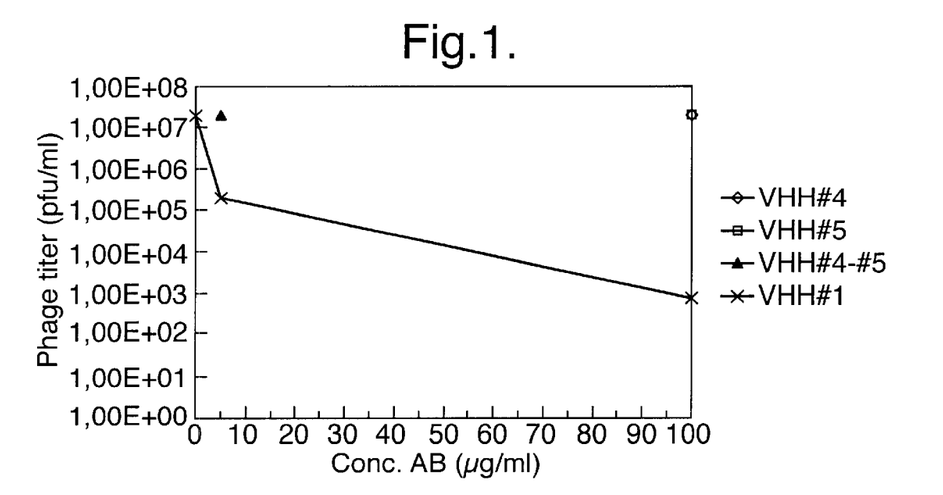
FIG. 1 shows the efficiency of the selected monovalent VHH fragment VHH#1 in neutralising *Lactococcus lactis* bacteriophage P2 as measured by plaque titration.

FIG. 1 shows that a concentration of 5 μg/ml $V_HH$ fragment VHH#1 gave a reduction of more than 99% in the phage titre relative to the titre found for the control where no antibody fragment was added to phage. An ELISA positive, lactococcus phage P2 specific $V_HH$ fragment selected from the same antibody library, which was classified as non-neutralising in the high-throughput screening assay, gave no detectable level of neutralisation, even at concentrations of 100 μg/ml. The bihead molecule VHH#4-#5 did not inhibit infection, at least when the phage P2 was present a such high titres; the example described below shows that the bihead molecule is effective at lower titres of phage.

The results demonstrates extremely efficient inhibition (neutralisation) of bacteriophage P2 by the monovalent fragments here described.

Figure 2:
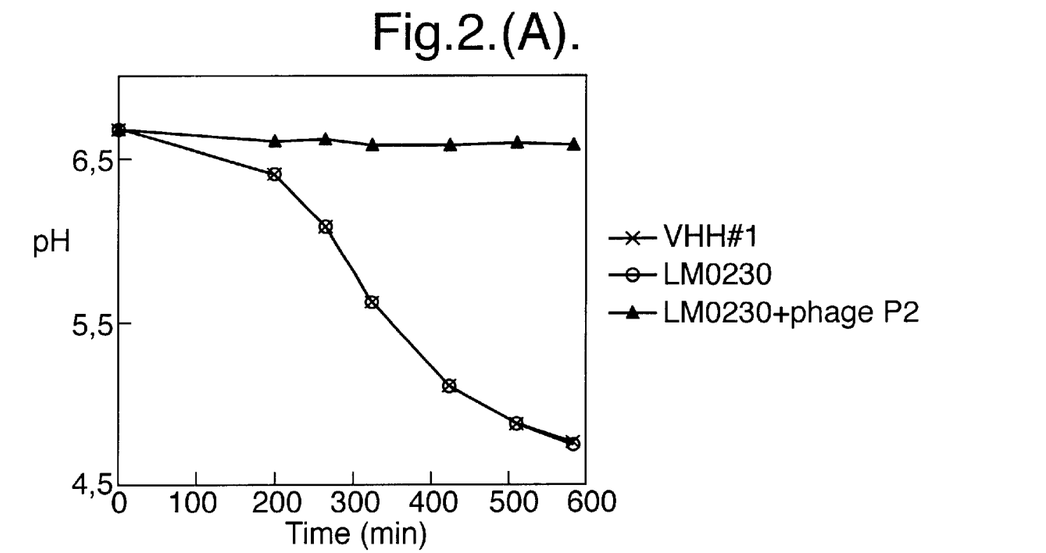
FIGS. 2A and 2B show the prevention of phage infection by VHH fragment VHH#1 in an acidification experiment with a small scale culture of milk.

3.4 The efficiency of phage neutralisation determined by the acidification of milk at 30 ml scale In a further aspect, the acidification of milk upon inoculation with lactic acid bacteria at 30° C. was followed by the regular measurement of the pH. For this purpose 30 ml XVM-glucose medium (skim milk solution containing 0.35% yeast extract, 0.35% peptone and 1% glucose) was inoculated with 300 µl of an overnight culture ($10^9$ cfu/ml) of *Lactococcus lactis* subsp. *cremoris* LM0230. Alternatively, strain C2 was used, which is the LM0230 derived strain producing protease, and therefore these bacteria can grow in skim milk without peptone and glucose. The cultures were incubated for 17 h at 30° C. after addition of variable amounts of purified $V_HH$ fragments. The XVM is acidified by the culture in a period of 8 hours (FIG. 2). When $10^3$ pfu/ml P2 phage was added to the culture of LM0230 or C2 in a parallel experiment, no acidification occurred during the whole period of 17 hours (FIG. 2, panel A and B). Addition of the monovalent antibody fragment VHH#1 (pUR3834) to the culture containing phage P2, resulted in a completely restored acidification profile (FIG. 2, panel A).

The bihead molecule VHH#4-#5 also prevented phage infection, but the neutralising character stemmed from its bivalency as could be concluded from experiments with the monovalent fragments VHH#4 and VHH#5, which as separately added fragments did not inhibit (FIG. 2, panel B).

Figure 3A:
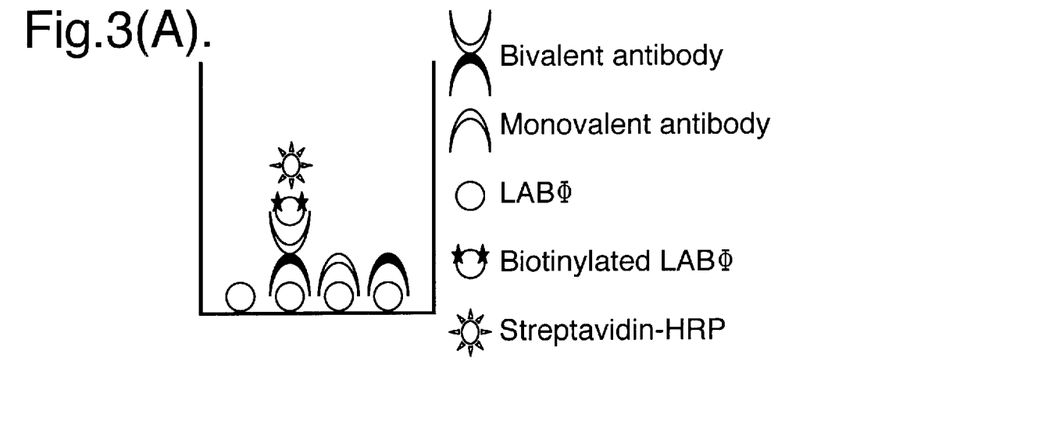
FIGS. 3A and 3B show the determination of the valency of the antibody fragments used in this study with an ELISA based method.
Figure 3B:
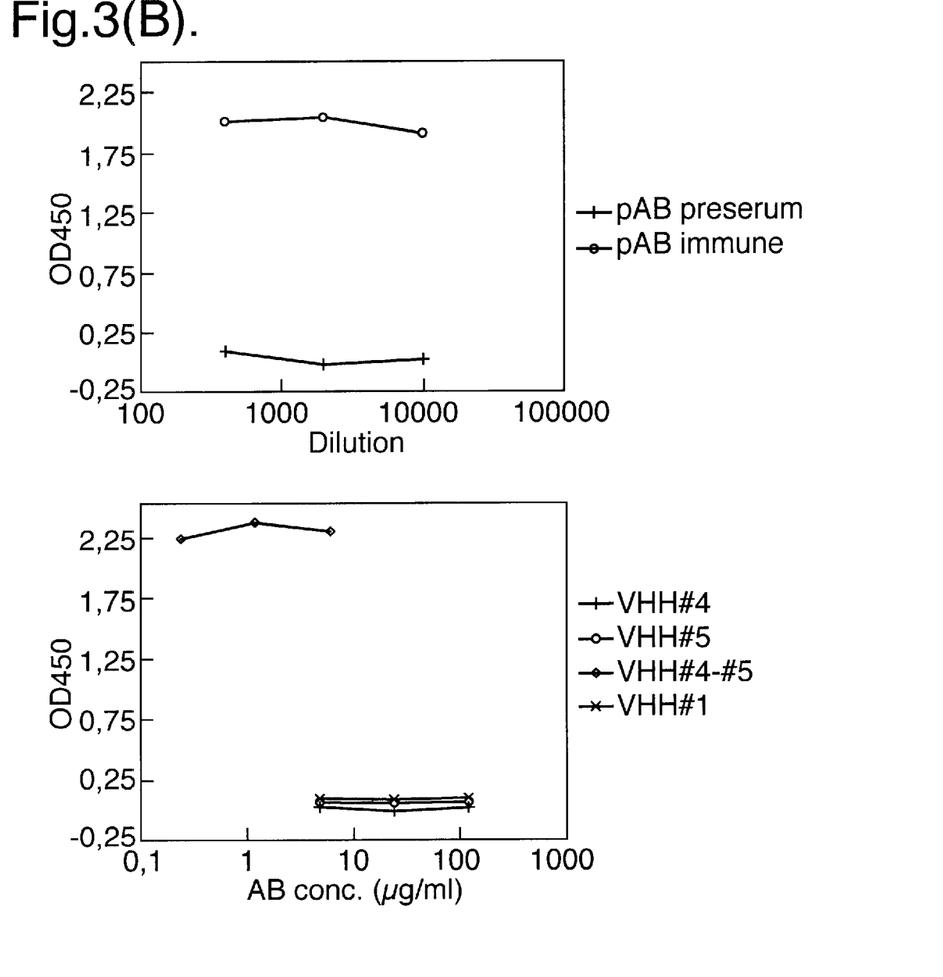

3.5 Conformation of the monovalent character of the phage neutralising $V_HH$ fragments In order to exclude possible aggregation of the $V_HH$ fragments, which might lead to the formation of dimers or higher orders of multimers, as has been observed for single chain antibodies (Hollinger et al (1993), Proc. Natl. Acad. Sci., 90, 6444–6448; Kortt et al (1997), Protein Eng., 10, 423–433), the produced molecules were analysed in an ELISA based test. In this assay bacteriophage was immobilised (at a concentration of $10^{10}$ pfu per ml of PBS) and as a detection probe in vitro biotinylated bacteriophage was used. Bivalent $V_HH$ fragment such as the bihead construct or polyclonal antibody (FIG. 3 panel B) present in sera from the immunised llama gave positive responses when incubated with biotinylated phage (prepared with NHS-biotin (Pierce) according to the instruction of the supplier) and horse radish peroxidase labelled streptavidin (DAKO); the principle of the assay is shown in FIG. 3 (panel A). In contrast, the non-neutralising $V_HH$ fragments VHH#4 and VHH#5 and the neutralising $V_HH$ fragments VHH#1, VHH#2 and VHH#3 as well as the polyclonal serum, taken from the llama prior to immunisation with bacteriophage, were not detected with biotinylated phage (FIG. 3, panel B).

These experiments showed that the produced $V_HH$ fragments are monomeric. Therefore the inhibiting effect is not obtained by cross-linking of bacteriophage particles, but rather is determined by the epitope(s) recognised by these particular antibodies.

3.6 Neutralisation of other species of Lactococcus phages

Lactococcus phages have been classified into 12 species. Of those only three species have been found to interfere with industrial milk fermentations, i.e. prolate headed c2 species and the isometric-headed 936 (most often found in factories) and P335 species. The bacteriophage P2, which was used for immunisation of the llama and selection of the antibody display library, belongs to the 936 species. Therefore the neutralising capacity of VHH#1 was examined against another member (phage SK1) of the 936 species, but also against two members (phage Q38 and c2) of the prolate headed c2 species.

With the microtiter plate assay described in example 2.3 the cross-reactivity and the neutralising capacity was analysed on the acidification of phage infected cultures as measure for phage resistance. To the mixture of host cells (at a density of $10^6$ cfu/ml) and bacteriophage (at a titer of $10^3$ pfu/ml) variable amounts of antibody fragment VHH#1 were added; after 15 hours of cultivation at 30° C. the neutralising activity could be observed by the colour change of the included indicator bromophenol red. The following combinations were tested: *L. lactis* strain C2 with phage P2, strain SMQ-196 and phage Q38 and bacterial strain LM230 with either phage SK1 or phage c2. Besides the described antibody fragment VHH#1 the polyclonal pre- and postimmune sera from the llama were used as negative and positive control as well as not-infected bacterial host.

The two tested phages p2 and SK1 of the isometric-headed 936 species were effectively neutralised by the monovalent antibody fragment (up to a dilution of 47 ng/ml) and post-immune serum (up to a $10^{-4}$ fold dilution). In contrast, the two members Q38 and c2 of the prolate-headed c2 species were not inhibited by VHH#1, not even at concentrations of 0.47 mg/ml, while some neutralisation was observed with post-immune serum at a 10-fold dilution.

By using this limited number of different phage types it was concluded that members of the isometric-headed species (used for immunisation) were neutralised effectively by VHH#1, but that phage belonging to the distantly related prolate-headed c2 species were not inhibited.

Example 4

Protecting a Cheese Starter Culture from Infection with Phage During the Production and the Ripening of Semi-hard Gouda Cheese Gouda-type cheeses were produced on pilot scale (200 L batches of cheese milk, yielding 4 cheeses of about 6 kg per batch) in open cheese vats. The cheese milk is treated by thermization (68° C., 14 sec) and bactofugation, before being standardised to achieve a cheese fat content of about 50% (dry matter). The milk subsequently is pasteurised for 10 sec at 72° C. To the cheese mil, the following components were added:

| | |
|---|---|
| At t = 0 min: | bacteriophage P2 in different levels (Table I) |
| At t = 5 min: | addition of $CaCl_2$ (23.1 g/100 l), $NaNO_3$ (15.5 g/100 l) and different levels of the monovalent antibody fragment VHH#1 |
| At t = 10 min: | addition of 450 g/100 l starter culture *Lactococcus lactis* C2 (fully grown in milk) |
| At t = 15 min: | addition of 23 g/100 l calf rennet |

All additions were poured in slowly to the stirred cheese milk to guarantee complete mixing. Further processing (renneting, cutting, curd washing, scalding, draining and filling) was carried out as usual for standard Gouda-type cheese, according to well-known processes as described by Kammerlehner (1) and by De Vries and Van Ginkel (2). Brining was started when the cheeses had reached a pH of 5.5 to 5.4. Cheeses were ripened at 13° C. at 88% relative humidity.

During ripening, samples were taken for the following analysis:

at 2 weeks for the general chemical analysis at 2, 6,13 weeks for protein degradation (total, soluble and amino acid nitrogen (3))

at 13 weeks for an extensive aroma analysis

Samples were stored frozen at −40° C. before analysis.

TABLE I

Compilation of the 3 separate cheese experiments performed

| Code | Phage (pfu/ml) | Phage in whey | VHH#1 (µg/ml) | VHH#1 in whey | pH (6 h; 24 h) |
|---|---|---|---|---|---|
| 1.1 | — | — | — | − | 5.40; 5.22 |
| 1.2 | — | — | 1 | + | 5.40; 5.21 |
| 1.3 | $1.0 \times 10^3$ | $2.2 \times 10^3$ | — | − | 6.00; 5.65 |
| 1.4 | $1.0 \times 10^3$ | — | 1 | + | 5.46; 5.19 |
| 1.5 | $1.2 \times 10^4$ | — | 1 | + | 5.40; 5.26 |
| 2.1 | — | — | — | − | 5.51; 5.16 |
| 2.2 | $1.8 \times 10^3$ | — | 0.1 | + | 5.59; 5.16 |
| 2.3 | $1.8 \times 10^4$ | — | 1 | + | 5.57; 5.18 |
| 2.4 | $2.1 \times 10^4$ | — | 0.1 | + | 5.53; 5.21 |
| 2.5 | $1.7 \times 10^3$ | $3.0 \times 10^3$ | — | − | 5.90; 5.58 |
| 3.1 | — | — | — | − | 5.44; 5.22 |
| 3.2 | $1.4 \times 10^3$ | — | 0.1 | + | 5.45; 5.20 |
| 3.3 | $1.3 \times 10^4$ | — | 1 | + | 5.49; 5.21 |
| 3.4 | $1.5 \times 10^5$ | — | 1 | + | 5.48; 5.21 |
| 3.5 | $1.8 \times 10^5$ | 27 | 0.1 | ???? | 5.45; 5.24 |

The results depicted in Table I clearly show that addition of the monovalent antibody fragment VHH#1 to the P2 phage infected cheese milk, prior to the addition of the starter culture L. lactis C2, protects the culture against phage infection. Phages are not detected anymore in the whey even if the cheese milk is infected with $1.5 \times 10^5$ pfu/ml, when 1 µg/ml of VHH#1 is present. The acidification of the cheese milk is as expected (cf. 3.1 with 3.4). When the antibody fragment is not added, phages are detected in the whey and the acidification slows down significantly (cf. 1.1 and 1.3 or 2.1 and 2.5). When the antibody fragment is added, the activity still can be found back in the whey, even if the phage is added prior to the antibody. This proves that the antibody is present in excess and is able to neutralise the phage completely. As can be seen from experiment 3.5, the limit is possibly reached when 0.1 µg/ml VHH#1 is added to cheese milk infected with $1.8 \times 10^5$ pfu/ml. This level of phage infection is considered to be extremely high in a normal operating cheese plant.

To determine if the neutralisation of the phage during the initial cheese fermentation is enough to obtain a normal cheese ripening process, the chemical composition of the cheeses has been determined after 2 weeks as well as the proteolysis after 2, 6 and 13 weeks (Table II and III).

TABLE II

Chemical composition cheeses after 2 weeks

| Analysis | % Humidity | % Fat | % Fat i.d.s. | % Salt | % Salt i.d.s. | pH |
|---|---|---|---|---|---|---|
| 1.1 | 41.4 | 29.6 | 50.4 | 1.9 | 3.1 | 5.17 |
| 1.2 | 41.6 | 29.4 | 50.3 | 1.9 | 3.2 | 5.16 |
| 1.3 | 40.9 | 29.9 | 50.4 | 2.3 | 3.9 | 5.63 |
| 1.4 | 40.1 | 29.6 | 50.2 | 1.9 | 3.3 | 5.18 |
| 1.5 | 41.5 | 29.9 | 51.0 | 1.8 | 3.1 | 5.14 |
| 2.1 | 42.5 | 29.2 | 50.9 | 2.2 | 3.8 | 5.13 |
| 2.2 | 41.2 | 29.7 | 50.6 | 2.2 | 3.7 | 5.14 |
| 2.3 | 41.2 | 30.0 | 51.0 | 2.2 | 3.7 | 5.15 |
| 2.4 | 39.7 | 30.9 | 51.0 | 1.8 | 3.0 | 5.19 |
| 2.5 | 39.6 | 31.2 | 51.4 | 1.8 | 3.0 | 5.60 |
| 3.1 | 42.3 | 30.0 | 51.7 | 1.7 | 3.0 | 5.16 |
| 3.2 | 41.7 | 30.3 | 51.8 | 1.7 | 2.9 | 5.17 |
| 3.3 | 41.4 | 30.2 | 51.4 | 1.6 | 2.8 | 5.19 |
| 3.4 | 40.4 | 30.5 | 51.0 | 1.5 | 2.6 | 5.22 |
| 3.5 | 40.4 | 31.1 | 51.8 | 1.8 | 2.8 | 5.26 |

TABLE III

Proteolysis during ripening of the cheeses (Soluble Nitrogen/Total Nitrogen; Amino acid Nitrogen/TN; AN/SN)

| | SN/T N | | | AN/T N | | | AN/ SN | | |
|---|---|---|---|---|---|---|---|---|---|
| Weeks | 2 | 6 | 13 | 2 | 6 | 13 | 2 | 6 | 13 |
| 1.1 | 7.70 | 11.80 | 17.19 | 1.39 | 2.13 | 2.78 | 18.06 | 18.08 | 16.19 |
| 1.2 | 7.86 | 12.31 | 17.47 | 1.53 | 2.23 | 2.90 | 19.50 | 18.14 | 16.62 |
| 1.3 | 7.36 | 11.33 | 15.33 | 2.61 | 4.25 | 5.79 | 35.42 | 37.53 | 37.76 |
| 1.4 | 7.60 | 12.34 | 19.32 | 2.15 | 2.47 | 3.39 | 28.32 | 20.0 | 17.55 |
| 1.5 | 7.81 | 12.94 | 17.76 | 1.63 | 2.65 | 4.11 | 20.92 | 20.48 | 23.17 |
| 2.1 | 6.77 | 10.71 | 14.96 | 1.94 | 2.02 | 2.75 | 28.69 | 18.87 | 18.39 |
| 2.2 | 6.75 | 11.48 | 16.14 | 1.65 | 2.10 | 3.37 | 24.48 | 18.33 | 20.90 |
| 2.3 | 6.11 | 11.95 | 16.72 | 1.84 | 2.93 | 3.83 | 30.13 | 24.50 | 22.90 |
| 2.4 | 6.72 | 11.42 | 17.15 | 2.00 | 2.28 | 3.60 | 29.77 | 19.96 | 20.98 |
| 2.5 | 7.53 | 12.01 | 16.92 | 2.93 | 4.30 | 6.16 | 38.87 | 35.76 | 36.44 |
| 3.1 | 8.33 | 12.49 | 17.28 | 1.13 | 1.86 | 2.65 | 13.51 | 14.86 | 15.36 |
| 3.2 | 7.72 | 12.60 | 17.51 | 1.33 | 2.09 | 3.10 | 17.27 | 16.63 | 17.68 |
| 3.3 | 8.25 | 12.33 | 17.75 | 1.47 | 2.22 | 3.81 | 17.78 | 18.05 | 21.05 |
| 3.4 | 8.21 | 12.90 | 18.95 | 1.58 | 2.75 | 4.42 | 19.20 | 21.32 | 23.33 |
| 3.5 | 7.96 | 12.39 | 18.34 | 1.49 | 2.59 | 4.34 | 18.77 | 20.93 | 23.68 |

From the data in Table II it can be concluded that the chemical composition of a cheese is not much influenced by the presence of a phage apart from the acidification (cf. 1.3 and 2.5 with the other data). Consequently an additional ripening period of 2 weeks, does not restore the acidification capacity of the starter culture upon infection with the phage, unless the neutralising antibody VHH#1 is added prior to the starter culture. The data from Table III show that proteolysis, that is one of the major indicative parameters for cheese ripening, is abnormal in phage infected cheeses and that this once again can be normalised if VHH#1 is added prior to the addition of the starter culture (cf. The AN/TN and AN/SN data of 1.3 and 2.5 with the other data). Too many amino acids are liberated when the phage is not neutralised by VHH#1, indicating an unbalanced proteolysis and therefore and off-flavoured cheese.

References

1. Kammerlehrer, J. (1989) Lab-Käse Technologie. Band III, p 642–643. In Molkereitechnik Band 84/85. Verlag Th. Mann, Gelsenkircher-Buer, ISBN 3-7862-0083-1

2. De. Vries E. and van Ginkel, W. (1980) Test of a curd-making tank. Type "Damrow Double O" with a capacity of 16000 L, manufactured by DEC. NIZO Rapport R113

3. Noomen, A., (1977) Noordhollandse Meshanger Cheese: a model for research on cheese ripening.2. The ripening of the cheese. Neth. Milk Diary J. 31, 75–102

What is claimed is:

1. A method of inhibiting viral infection using a monovalent antigen binding protein comprising a single variable domain binding unit, or a functional equivalent thereof, capable of binding to a virus and contacting said protein with said virus to bind the virus and inhibit infection thereby.

2. A method according to claim 1 wherein the single domain variable domain binding unit comprises a heavy chain variable domain derived from an immunoglobulin devoid of light chains, or a functional equivalent thereof.

3. A method according to claim 2 wherein the single variable domain binding unit comprises a heavy chain variable domain derived from a Camelid immunoglobulin or a functional equivalent thereof.

4. A method according to claim 1 wherein the virus is a lactococcal bacteriophage.

5. A method according to claim 1 wherein the virus is pathogenic to humans or animals.

6. A method according to claim 1 wherein the virus is pathogenic to plants.

7. A method according to claim 1 wherein the monovalent antigen-binding protein comprises a heavy chain variable domain including an amino acid sequence as shown in SEQ. ID NO. 1, 2 or 3.

* * * * *

SEQUENCE LISTING

<160> NUMBER OF SEQ ID NOS: 8

<210> SEQ ID NO 1
<211> LENGTH: 123
<212> TYPE: PRT
<213> ORGANISM: LLAMA

<400> SEQUENCE: 1

```
Gln Val Gln Leu Gln Glu Ser Gly Gly Gly Leu Val Gln Ala Gly Gly
 1               5                  10                  15

Ser Leu Arg Leu Ser Cys Thr Ala Ser Arg Arg Thr Gly Ser Asn Trp
            20                  25                  30

Cys Met Gly Trp Phe Arg Gln Leu Ala Gly Lys Glu Pro Glu Leu Val
        35                  40                  45

Val Ala Leu Asn Phe Asp Tyr Asp Met Thr Tyr Tyr Ala Asp Ser Val
    50                  55                  60

Lys Gly Arg Phe Thr Val Ser Arg Asp Ser Gly Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Arg Ser Gly Gly Phe Ser Ser Asn Arg Glu Leu Tyr Asp Gly
            100                 105                 110

Trp Gly Gln Gly Thr Gln Val Thr Val Ser Ser
        115                 120
```

<210> SEQ ID NO 2
<211> LENGTH: 123
<212> TYPE: PRT
<213> ORGANISM: LLAMA

<400> SEQUENCE: 2

```
Gln Val Gln Leu Gln Glu Ser Gly Gly Gly Leu Val Gln Ala Gly Gly
 1               5                  10                  15

Ser Leu Arg Leu Ser Cys Thr Ala Ser Arg Arg Thr Gly Ser Asn Trp
            20                  25                  30

Ser Met Gly Trp Phe Arg Gln Leu Ala Gly Lys Glu Arg Glu Phe Val
        35                  40                  45

Val Ala Leu Asn Leu Asp Tyr Asp Ile Pro Tyr Tyr Ala Asp Ser Val
    50                  55                  60

Lys Gly Arg Phe Thr Val Ser Thr Asp Ser Gly Lys Asn Thr Val Tyr
65                  70                  75                  80

Leu Gln Met Asn Ser Leu Lys Pro Glu Asp Thr Ala Ile Tyr Phe Cys
                85                  90                  95

Ala Ala Arg Ser Gly Gly Phe Ser Ser Asn Arg Thr Tyr Tyr Asp Tyr
            100                 105                 110

Trp Gly Gln Gly Thr Gln Val Thr Val Ser Ser
        115                 120
```

<210> SEQ ID NO 3
<211> LENGTH: 123
<212> TYPE: PRT
<213> ORGANISM: LLAMA

<400> SEQUENCE: 3

```
Gln Val Gln Leu Gln Gln Ser Gly Gly Gly Leu Val Gln Arg Gly Gly
 1               5                  10                  15
```

```
Ser Leu Arg Leu Ser Cys Thr Ala Ser Arg Arg Thr Gly Ser Asn Trp
             20                  25                  30

Ser Met Gly Trp Phe Arg Gln Phe Ala Gly Lys Glu Pro Asp Leu Leu
         35                  40                  45

Val Ala Leu Asn Leu Asp Tyr Asp Val Pro Tyr Tyr Ala Asp Ser Val
     50                  55                  60

Lys Gly Arg Phe Thr Val Ser Gly Asp Ser Gly Lys Asn Thr Val Tyr
 65                  70                  75                  80

Leu Gln Met Asn Leu Lys Pro Glu Asp Thr Ala Ile Tyr Tyr Cys
                 85                  90                  95

Ala Ala Arg Ser Gly Gly Phe Ser Ser Asn Arg Ala Leu Tyr Asp Gly
             100                 105                 110

Trp Gly Gln Gly Thr Gln Val Thr Val Ser Ser
             115                 120
```

```
<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:PRIMER

<400> SEQUENCE: 4
aggtsmarct gcagsagtcw gg                                          22

<210> SEQ ID NO 5
<211> LENGTH: 53
<212> TYPE: DNA
<213> ORGANISM: Artificial Sequence
<220> FEATURE:
<223> OTHER INFORMATION: Description of Artificial Sequence:PRIMER

<400> SEQUENCE: 5
aacagttaag cttccgcttg cggccgcgga gctggggtct tcgctgtggt gcg        53

<210> SEQ ID NO 6
<211> LENGTH: 53
<212> TYPE: DNA
<213> ORGANISM: Artificial Sequence
<220> FEATURE:
<223> OTHER INFORMATION: Description of Artificial Sequence:PRIMER

<400> SEQUENCE: 6
aacagttaag cttccgcttg cggccgctgg ttgtggtttt ggtgtcttgg gtt        53

<210> SEQ ID NO 7
<211> LENGTH: 121
<212> TYPE: PRT
<213> ORGANISM: LLAMA

<400> SEQUENCE: 7

Gln Val Gln Leu Gln Glu Ser Gly Gly Gly Leu Val Gln Pro Gly Gly
  1               5                  10                  15

Ser Leu Arg Leu Ser Cys Val Val Ser Gly Glu Gly Phe Ser Asn Tyr
             20                  25                  30

Pro Met Gly Trp Tyr Arg Gln Ala Pro Gly Lys Gln Arg Glu Leu Val
         35                  40                  45

Ala Ala Met Ser Glu Gly Gly Asp Arg Thr Asn Tyr Ala Asp Ala Val
     50                  55                  60

Lys Gly Arg Phe Thr Ile Ser Arg Asp Asn Ala Lys Lys Thr Val Tyr
 65                  70                  75                  80
```

```
Leu Gln Met Ser Ser Leu Lys Pro Glu Asp Thr Ala Val Tyr Tyr Cys
                85                  90                  95

Asn Ala Ala Arg Trp Asp Leu Gly Pro Ala Pro Phe Gly Ser Trp Gly
            100                 105                 110

Gln Gly Thr Gln Val Thr Val Ser Ser
        115                 120

<210> SEQ ID NO 8
<211> LENGTH: 113
<212> TYPE: PRT
<213> ORGANISM: LLAMA

<400> SEQUENCE: 8

Gln Val Gln Leu Gln Glu Ser Gly Gly Gly Leu Val Gln Pro Gly Gly
 1               5                  10                  15

Ser Leu Arg Leu Ser Cys Ala Val Ser Gly Ala Pro Phe Arg Glu Ser
            20                  25                  30

Thr Met Ala Trp Tyr Arg Gln Thr Pro Gly Lys Glu Arg Glu Thr Val
            35                  40                  45

Ala Phe Ile Thr Ser Gly Gly Ser Lys Thr Tyr Gly Val Ser Val Gln
        50                  55                  60

Gly Arg Phe Thr Ile Ser Arg Asp Ser Asp Arg Arg Thr Val Leu Leu
 65                  70                  75                  80

Gln Met Asn Asn Leu Gln Pro Glu Asp Thr Ala Val Tyr Tyr Cys His
                85                  90                  95

Arg Ala Leu Ser Asn Thr Trp Gly Gln Gly Ile Gln Val Thr Val Ser
            100                 105                 110

Ser
```